United States Patent [19]

Thomas et al.

[11] Patent Number: 5,120,884
[45] Date of Patent: Jun. 9, 1992

[54] PREPARATION OF HYDROXY ARYLCYCLOBUTENES

[75] Inventors: P. J. Thomas; R. Garth Pews, both of Midland, Mich.

[73] Assignee: The Dow Chemical Company, Midland, Mich.

[21] Appl. No.: 655,875

[22] Filed: Feb. 14, 1991

[51] Int. Cl.$^5$ .............................. C07C 39/14
[52] U.S. Cl. ..................... 568/734; 568/803
[58] Field of Search ................ 568/734, 803

[56] References Cited

U.S. PATENT DOCUMENTS

| | | |
|---|---|---|
| 1,842,989 | 1/1932 | Kropp et al. |
| 1,882,825 | 10/1932 | Hale et al. |
| 3,234,291 | 2/1966 | Kelly |
| 3,585,243 | 6/1971 | Gradeff |
| 3,849,502 | 11/1974 | Bourdin et al. |
| 3,872,156 | 3/1975 | Bourdin et al. |
| 3,875,247 | 4/1975 | Bourdin et al. |
| 3,927,122 | 12/1975 | Bourdin et al. |
| 4,018,833 | 4/1977 | Muller et al. |
| 4,094,912 | 6/1978 | Feinstein et al. |
| 4,174,460 | 11/1979 | Seifert et al. |
| 4,334,108 | 6/1982 | Hashimoto et al. |

OTHER PUBLICATIONS

Organic Reactions, vol. IX, Robert E. Krieger Publishing Co. Huntington, NY, 1975, pp. 84–85.
March, "Advanced Organic Chemistry: Reactions, Mechanisms and Structure," 2d Ed., McGraw-Hill Book Co., NY, pp. 1011–1012.
Ogata et al, "Kinetics of the Baeyer–Villiger Reaction of Acetophenones with Permonophosphoric Acid," J. Org. Chem. vol. 43, No. 12, 1978, pp. 2417–2419.
Lloyd et al., "The Electrophilic Substitution of Benzocyclobutene-III," Tetrahedron, 1965, vol. 21, pp. 2281–2288, Pergamon Press Ltd, printed in Northern Ireland.

*Primary Examiner*—Asok Pal
*Assistant Examiner*—P. N. Achutamurthy
*Attorney, Agent, or Firm*—John A. Gazewood; Charles J. Enright

[57] ABSTRACT

Hydroxy arylcyclobutenes are prepared by the Baeyer–Villiger oxidation of arylcyclobutene aldehydes with permonophosphoric acid.

14 Claims, No Drawings

PREPARATION OF HYDROXY ARYLCYCLOBUTENES

BACKGROUND OF THE INVENTION

The present invention relates to a process for the preparation of hydroxy arylcyclobutene.

In recent years, the search for high-performance materials, especially high temperature-resistant polymers, has gained momentum. In order for material to have stability at high temperatures, it must fulfill several requirements, including a high melting or softening temperature, a high modulus or rigidity, a resistance to solvent and chemical degradation and toughness. The intrinsic thermal and oxidative stability of aromatic structures has long been recognized, and a variety of polymers have been made in which benzene rings are linked together by various connecting groups.

Aromatic hydrocarbons which have cyclobutene rings fused to the aromatic nucleus are useful in the preparation of high-performance polymers. These high-performance polymers exhibit thermal stability at elevated temperatures, chemical resistance to most conventional solvents, good mechanical and electrical properties, and low sensitivity to water. They are useful as films, advanced composites, adhesives, structural laminates, matrix resins, and planarization resins for the electronics and aerospace industries.

The cyclobutene-substituted aromatic hydrocarbons are also suitable for preparing aromatic ring-substituted intermediates which are themselves polymerizable or can be used to introduce the polymerizable arylcyclobutene moiety into a variety of monomers and polymers to enhance heat resistance of the ultimate products. It is, however, quite difficult to introduce reactive groups such as hydroxy and amine groups onto the aromatic nucleus of arylcyclobutene compounds because severe reaction conditions which are often required for such nuclear substitutions result in an undesired opening of the cyclobutene ring. In addition, yields of the desired product are generally too low for commercial acceptability.

The Baeyer-Villiger rearrangement is a known reaction for oxidizing ketones and aldehydes with peracids to provide the corresponding alcohol or carboxylic acid. Ogata et al, "Kinetics of the Baeyer-Villiger Reaction of Acetophenones With Permonophosphoric Acid", *J. Orq. Chem.*, Vol. 43 (12), 1978, 2417-2419 disclose the oxidation of acetophenones with permonophosphoric acid in the presence of a strong acid catalyst such as sulfuric acid. For example, phenols can be obtained by oxidizing aldehydes either by using organic peracids, such as peracetic or perbenzoic acid, or by using hydrogen peroxide as the oxidizing agents. When a peracid is used, the Baeyer-Villiger reaction leads, as a general rule, almost quantitatively to a phenol if the starting aldehyde contains an electron donor substituent, such as a hydroxyl or alkoxy group. Exceptions to this rule have been reported. Even though the methyl and other alkyl groups are considered to be electron donor groups, para-tolualdehyde gives p-toluic acid when oxidized by perbenzoic acid. 4-methoxy-benzaldehyde is oxidized quantitatively to 4-methoxy-benzoic acid by peracetic acid in aqueous alcohol.

Further, if the starting aldehyde contains an electron acceptor substituent, such as $NO_2$, methylcarbonyloxy or halogen group, or if it is unsubstituted, such as benzaldehyde, the reaction leads to the preferential formation of the corresponding benzoic acid. For example, benzaldehyde has been oxidized quantitatively to benzoic acid by peracetic acid and by perbenzoic acid.

When hydrogen peroxide is used as the oxidizing agent, and the reaction is carried out in a neutral aqueous or in an organic solvent medium, the acid corresponding to the starting aldehyde is obtained as the principal or exclusive reaction product, with phenol being obtained in low yields in some cases. For example, the oxidation of various methoxy-benzaldehydes and of benzaldehyde itself using hydrogen peroxide in ether leads to low yields of the phenols. When hydrogen peroxide is used in an alkaline medium, a phenol is generally obtained when a substituted benzaldehyde containing at least one hydroxyl group is used as the starting material, and an acid is generally obtained when an aldehyde which does not contain such a substituent is used as the starting material.

Based on the foregoing techings, one would not expect to obtain quantitatively significant yields of hydroxyarylcyclobutenes using the Baeyer-Villiger rearrangement on arylcyclobutene aldehydes.

SUMMARY OF THE INVENTION

The present invention surprisingly provides a method for preparing hydroxy arylcyclobutene by treating the corresponding arylcyclobutene aldehyde with permonophosphoric acid. The treatment of the arylcyclobutene aldehyde with permonophosphoric acid in accordance with the present invention is highly selective to hydroxy arylcyclobutene with insignificant, if any, amounts of the corresponding arylcyclobutene carboxylic acid.

DESCRIPTION OF THE PREFERRED EMBODIMENTS

The arylcyclobutene moiety can be any aromatic radical which has at least one cyclobutene ring fused to at least one aromatic ring. The term "aryl" refers herein to any aromatic radical. "Aromatic" as used herein refers to carbocyclic or heterocyclic rings in which (4N+2) delocalized pi electrons are contained in an orbital ring, as described in Morrison and Boyd, *Orqanic Chemistry*, 3d ed., 1973. This property is also known as "resonance stabilization" or "delocalization". Preferred carbocyclic aromatic radicals include benzene, naphthalene, phenanthrene, anthracene, pyridine, biaryl moieties, or two or more aromatic radicals bridged by alkylene or cycloalkylene moieties. More preferred carbocyclic aromatic radicals include benzene, naphthalene, biphenyl, binaphthyl, or a diphenyl alkylene or a diphenyl cycloalkylene compound. The most preferred carbocyclic aromatic radical is benzene. Examples of preferred heterocyclic aromatic radicals include pyrrole, furan, thiophene, imidazole, oxazole, thiazole, pyrazole, pyridine, and pyrimidine. More preferred heterocyclic aromatic compounds are pyridine, furan and thiophene, with pyridine being most preferred. The carbocyclic aromatic rings are preferred over the heterocyclic aromatic rings. Except for the fused butene ring, the sole substituent on the aromatic nucleus is the aldehyde group —CHO, which is preferably in a meta position with respect to at least one of the cyclobutene carbon atoms.

The arylcyclobutene aldehydes which are converted to the corresponding hydroxy arylcyclobutenes in accordance with the invention correspond to the formula:

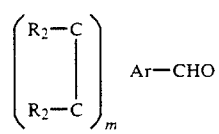

wherein;
Ar is an aryl moiety; R is separately and independently in each occurrence hydrogen, an electron-donating moiety or an electron-withdrawing moiety; and m is an integer of at least 1. Separately and independently in each occurrence means that R can be the same or different in each occurrence.

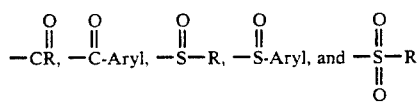

The cyclobutene ring or rings may be substituted with electron-withdrawing groups or electron-donating groups. Electron-donating moieties are molecular or nuclear groups which donate electrons more than a hydrogen atom would if accompanying the same site. Electron-withdrawing moieties are groups which more readily withdraw an electron relative to a hydrogen atom. Examples of suitable electron-withdrawing moieties include $-NO_2$, $-CN$, Br, I, Cl, F, $-PR_2$, $-CO_2H$, $-CO_2R$, t,61
and aryl. Examples of suitable electron donating groups include alkyl, aryl, alkoxy, aryloxy, hydrocarbyl, hydrocarbyloxy, hydrocarbylthio, $-OH$, $-OR$, $-NH_2$, $-NHR$, $-NR_2$. Hydrocarbyl refers to any organic moiety containing carbon and hydrogen atoms; hydrocarbyloxy refers to such organic moieties which further contain a hydroxyl moiety; and hydrocarbylthio refers to organic moieties which further contain a sulfur atom. Preferred substituents on the cyclobutene ring are cyano, carboxylate, hydrocarbylcarbonyloxy, nitro, halo and hydrocarbylthio. More preferred substituents include halo, nitro or cyano groups, with cyano groups being most preferred.

While the invention is thus broadly applicable to the conversion of arylcyclobutene aldehydes to hydroxy arylcyclobutenes, the invention will be specifically described with respect to the particularly preferred embodiment, that is, the conversion of 3-benzocyclobutene aldehyde to 3-hydroxybenzocyclobutene, or 3-benzocyclobutene phenol as it might also be identified. The most precise momenclature for this compound appears to be 3-hydroxy, bicyclo[4.2.0]-octa-1,3,5-triene. These terms will be used interchangeably herein to refer to the same compound.

In the preferred embodiment process of this invention, benzocyclobutene aldehyde is contacted with permonophosphoric acid, preferably in the presence of an inert organic reaction medium, whereby the benzocyclobutene aldehyde is oxidized to hydroxy benzocyclobutene:

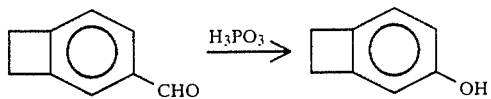

Permonophosphoric acid is, like perbenzoic acid, peracetic acid and peroxytrifluoroacetic acid, a peroxy acid which is utilized as an oxidizing agent. It is readily prepared from phosphorous pentoxide and hydrogen peroxide, preferably in an organic solvent such as acetonitrile. In forming the permonophosphoric acid, substantially equivalent amounts of phosphorous pentoxide and hydrogen peroxide are preferably employed.

The benzocyclobutene aldehyde is readily prepared from benzocyclobutene monomer by contacting benzocyclobutene with dichloromethyl methyl ether in the presence of titanium tetrachloride to directly form 3-benzocyclobutene aldehyde. Alternatively, benzocyclobutene can be brominated to a 3-bromobenzocyclobutene, which can be converted by grignard synthesis to the benzocyclobutene aldehyde.

The oxidation of 3-benzocyclobutene aldehyde with permonophosphoric acid is effected at moderate temperatures, preferably in the range from 0° to 32° C. Excessive temperatures should be avoided because of the tendency of 3-hydroxybenzocyclobutene to undergo an opening of the cyclobutene ring at elevated temperatures in the presence of strong acids such as the permonophosphoric acid. The reaction is preferably effected in the presence of organic solvents which are inert with respect to the reactants. Suitable solvents include 1,2-dichloroethane, methylene chloride, acetonitrile and methylene dichloride, with acetonitrile being a particularly preferred solvent. Typically, at least stoichiometric quantities of the 3-benzocyclobutene aldehyde and permonophosphoric acid are employed. However, it is currently preferred to conduct the oxidation using from two to three equivalents of permonophosphoric acid per equivalent of 3-benzocyclobutene aldehyde.

Following the reaction, the reaction mixture is preferably lowered to a temperature on the order of about 0° C. and any excess permonophosphoric acid is destroyed, for example, by adding a reducing agent such as sodium bisulfite. The organic solvent is then preferably removed and the reaction product is made alkaline, for example, with sodium hydroxide solution, cooled to 0° C., acidified and extracted with ethyl acetate. The organic layer is then typically washed with water, sodium bicarbonate and brine. After solvent removal, the product can be recovered by either distillation under reduced pressure or recrystallation.

The following examples are included for illustrative purposes only, and do not limit the scope of the invention or claims. Unless otherwise stated, all parts and percentages are by weight except yields are given in mole percent.

EXAMPLE 1

Preparation of Hydroxybenzocvclobutene

A suspension of phosphorus pentoxide (14.2 g, 0.10 mole) in acetonitrile (60 mL) was added to a flask equipped with ice bath, stirrer and water-cooled condenser. To the stirred suspension was added a 70 percent solution of hydrogen peroxide (10 g, 0.20 mole) in acetonitrile (20 mL). The mixture was slowly warmed up to room temperature and stirred for 16 hours. Initially, a milky white solution formed which slowly turned into a colorless liquid.

A solution of the thus prepared permonophosphoric acid (18 mL, 1.2M) in acetonitrile was added to a flask equipped with ice bath, stirrer and water-cooled condenser. To the stirred solution was added 3-benzocyclobutene aldehyde (5 g, 0.037 moles) dropwise over a period of 30 minutes. The reaction mixture was stirred for an additional 2 hours and cooled to 0° C. Water (20 mL) was added to the cooled reaction mixture, followed by the addition of sodium bisulfite solution until the reaction mixture was free from permonophosphoric acid, as tested with starch iodide paper. The organic solvent was removed by rotary evaporation, and sodium hydroxide was added until the reaction mixture became alkaline. The reaction mixture was cooled to 0° C., acidified and extracted with ethyl acetate. The organic layer was washed with water, sodium bicarbonate and brine. Drying and removal of the solvent was followed by flash chromatography using 10 percent ethyl acetate in hexanes to afford 3.19 g 3-hydroxybenzocyclobutene as a solid. This represents a yield of approximately 70 percent. The 3-benzocyclobutene phenol was recrystallized from pentane. The 3-benzocyclobutene phenol product has a melting point of 47° C. Product analysis indicated substantially complete conversion of 3-benzocyclobutene aldehyde with the product, other than the desired 3-hydroxybenzocyclobutene, comprising unidentified polymer-like substance with substantially no formation of 3-benzocyclobutene carboxylic acid.

EXAMPLE 2 Comparative Example

Oxidation of Benzocyclobutene Aldehyde With Hydrogen Peroxide in the Presence of Acetic Acid and Sulfuric Acid Not an Example of the Invention A solution of benzocyclobutene aldehyde (0.5 g) in acetic acid (5 mL) was added to a flask equipped with ice bath, stirrer and water-cooled condenser. To the stirred solution at room temperature one drop of sulfuric acid was added, followed by the dropwise addition of 0.4 grams of hydrogen peroxide. After the addition of hydrogen peroxide was completed, the reaction mixture was stirred for 18 hours. The progress of the reaction was monitored by liquid chromatographic analysis, with the aldehyde being substantially completely consumed after 18 hours. A considerable amount of solid material formed during the reaction period.

The reaction mixture was poured into ice cold water, basified with sodium hydroxide solution and reacidified with dilute hydrochloric acid. The aqueous solution was extracted with methylene chloride. The organic layer was washed with brine, dried over anhydrous magnesium sulfate and the solvent was removed by evaporation. Total weight of material recovered from the reaction was 280 milligrams (approx. 56 wt. % recovery). Liquid chromatographic analysis of the reaction product found less than 5 percent hydroxy benzocyclobutene and 26 percent benzocyclobutene carboxylic acid, with the balance (approx. 61%) comprising unidentified materials characterized as mostly ring opened product.

EXAMPLE 3 Comparative Example

Oxidation of Benzocyclobutene Aldehyde With Hydrogen Peroxide in the Presence of Trifluoroacetic Anhydride and Methylene Chloride Not an Example of the Invention To a solution of trifluoroacetic anhydride (4.2 g) in 10 mL methylene chloride at 0° C. was slowly added 0.5 g of hydrogen peroxide. The mixture was stirred for 15 minutes at 0° C. To this solution was added 0.5 g benzocyclobutene aldehyde dissolved in methylene chloride. The reaction mixture was slowly warmed up to room temperature and stirred for 24 hours at room temperature. The progress of the reaction was monitored by liquid chromatographic analysis, with the aldehyde being substantially completely consumed after this period.

The reaction mixture was poured into ice cold water, excess peracid was destroyed with sodium bisulfite solution, the reaction mixture was basified with sodium hydroxide solution and the mixture was reacidified with dilute hydrochloric acid. The aqueous solution was extracted with methylene dichloride. The organic layer was washed with brine, dried over anhydrous magnesium sulfate and the solvent was removed by evaporation. Total weight of material recovered from the reaction was 100 milligrams (approx. 20 wt. % recovery). Liquid chromatographic analysis of the reaction product found approximately 16 percent yield to hydroxy benzocyclobutene and a trace amount of benzocyclobutene carboxylic acid, with the balance comprising unidentified materials characterized as undesired product.

EXAMPLE 4 COMPARATIVE EXAMPLE

Oxidation of Benzocyclobutene Aldehyde With Sodium Perborate in the Presence of Trifluoroacetic Acid and Methylene Dichloride Note an Example of the Invention Benzocyclobutene aldehyde (0.5 g), sodium perborate (1.7 g), trifluoroacetic acid (1 mL) and methylene dichloride (20 mL) were combined into a reaction flask such as described in the preceding examples. The mixture was stirred at room temperature for about 8 hours. The reaction was still incomplete, but there was recovered both benzocyclobutene carboxlic acid and hydroxy benzocyclobutene, with benzocyclobutene carboxylic acid comprising about 80 percent of the product.

EXAMPLE 5 COMPARATIVE EXAMPLE

Oxidation of Benzocyclobutene Aldehyde With Sodium Perborate

Not an Exammle of the Invention

Benzocyclobutene aldehyde (0.5 g) was added at room temperature to a stirred reaction flask similar to that described in the preceding examples containing a mixture of sodium perborate (2.5 g), trifluoroacetic acid (10 mL) and acetic acid (1.0 mL). Stirring was continued at room temperature for 18 hours. The reaction was monitored by liquid chromatographic analysis, with the aldehyde being substantially completely consumed after 18 hours.

The reaction mixture was poured into ice cold water, excess peracid was destroyed with sodium bisulfite solution and the reaction mixture was basified with sodium hydroxide solution. The mixture was cooled to 0° C. and acidified with dilute hydrochloric acid. The aqueous solution was extracted with methylene chloride. The organic layer was washed with water and brine, and the solvent was removed by evaporation. Total weight of material recovered from the reaction was 220 milligrams (approx. 44 wt. % recovery). Liquid chromatographic analysis of the reaction product found no hydroxy benzocyclobutene and less than 5 percent benzocyclobutene carboxylic acid, with the balance (approx. 95%) comprising unidentified materials characterized as undesired product.

EXAMPLE 6 COMPARATIVE EXAMPLE

Oxidation of Benzaldehyde With Permonophosphoric Acid

Not an Example of the Invention

Permonophosphoric acid was prepared following the procedure of Example 1 from 7.1 g phosphorous pentoxide and 5 g, 70 percent hydrogen peroxide in 60 mL acetonitrile. The resulting solution of permonophosphoric acid was cooled to 0° C. and 2.0 g of benzaldehyde was added to the stirred solution. The reaction mixture was warmed up to room temperature and stirred for an additional 4 hours. The product was worked up following the procedure of Example 1. Gas chromatographic analysis identified both benzoic acid and phenol, with benzoic acid comprising about 80 percent of the product.

EXAMPLE 7 OXIDATION OF BENZOCYCLOBUTENE

Not an Example of the Invention

3-Chloroperoxybenzoic acid (0.66 g) was added to a solution of benzocyclobutene aldehyde (0.2 g) in methylene chloride (10 mL) at 0° C. The mixture was stirred for 30 minutes at 0° C. and then warmed to room temperature. Stirring was continued for 12 hours at room temperature. Potassium floride (0.3 g) was added and stirring continued for an additional two hours. The reaction mixture was filtered, washed with sodium bisulfite solution and the solvent was removed by flash column chromatography. Liquid chromatographic analysis found a yield to hydroxy benzocyclobutene of approximately 55 percent and no benzocyclobutene carboxylic acid, with the balance comprising unidentified materials characterized as undesired product.

The above description is considered that of the preferred embodiment only. Modifications of the invention will occur to those who make or use the invention. Therefore, it is understood that the embodiment described above is merely for illustrative purposes and is not intended to limit the scope of the invention, which is defined by the following claims as interpreted according to the principles of patent law, including the doctrine of equivalence.

The embodiments of the invention in which an exclusive property or privilege is claimed are defined as 1. A method for preparing hydroxy arylcyclobutenes comprising oxidizing at least one arylcyclobutene aldehyde with permonophosphoric acid.

2. A method in accordance with claim 1 wherein said oxidation is effected at a temperature in the range from about 0° to about 32° C.

3. A method in accordance with claim 2 wherein said oxidation is effected at room temperature.

4. A method in accordance with claim 1 wherein said arylcyclobutene aldehyde comprises benzocyclobutene aldehyde and said hydroxy arylcyclobutene comprises hydroxybenzocyclobutene.

5. A method in accordance with claim 2 wherein benzocyclobutene aldehyde is oxidized to hydroxybenzocyclobutene.

6. A method in accordance with claim 5 wherein said oxidation is effected at room temperature.

7. A method in accordance with claim 1 wherein said arylcyclobutene aldehyde has the formula:

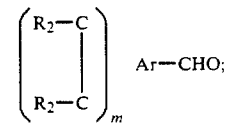

wherein Ar is an aryl moiety, R is separately and independently in each occurrence hydrogen, an electron-donating moiety or an electron-withdrawing moiety; and m is an integer of at least one.

8. A method in accordance with claim 7 wherein said oxidation is effected in the presence of at least stoichiometric quantities of said arylcyclobutene aldehyde and said permonophosphoric acid.

9. A method in accordance with claim 7 wherein said oxidation is effected in the presence of at least two equivalents of permonophosphoric acid per equivalent of arylcyclobutene aldehyde.

10. A method in accordance with claim 8 wherein said oxidation is effected at a temperature in the range from about 0° C. to about 32. C.

11. A method according to claim 10 wherein said oxidation is effected at room temperature.

12. A method in accordance with claim 9 wherein said oxidation is effected at a temperature in the range from about 0° C. to about 32 C.

13. A method in accordance with claim 12 wherein said oxidation is effected at room temperature.

14. A method according to claim 13 wherein said arylcyclobutene aldehyde comprises 3-benzocyclobutene aldehyde and said hydroxy arylcyclobutene comprises 3-hydroxybenzocyclobutene.

* * * * *

UNITED STATES PATENT AND TRADEMARK OFFICE
CERTIFICATE OF CORRECTION

PATENT NO. : 5,120,884
DATED : June 9, 1992
INVENTOR(S) : P. J. Thomas and R. Garth Pews It is certified that error appears in the above-identified patent and that said Letters Patent is hereby corrected as shown below:

Column 8, lines 25 to 30, delete

" 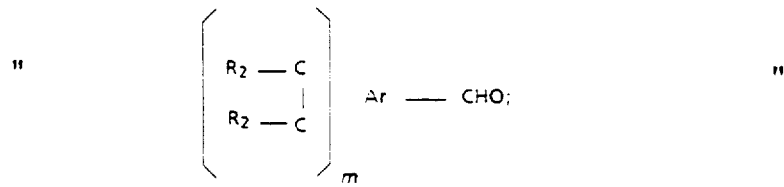 "

and insert

-- 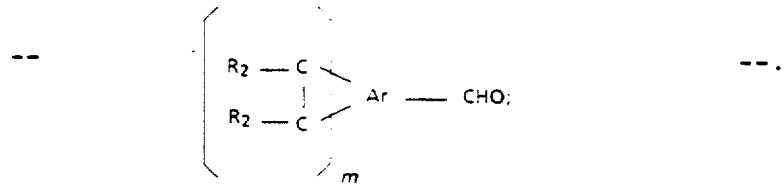 --.

Signed and Sealed this

Fourteenth Day of December, 1993

Attest:

BRUCE LEHMAN

*Attesting Officer*    *Commissioner of Patents and Trademarks*